(12) United States Patent
Hille et al.

(10) Patent No.: US 11,058,499 B2
(45) Date of Patent: Jul. 13, 2021

(54) ROBOTIC SURGICAL SYSTEM

(71) Applicant: avateramedical GmbH, Jena (DE)

(72) Inventors: Leander Hille, Jockgrim (DE); Tobias Luksch, Ruelzheim (DE); Ricardo A. Tauro, Karlsruhe (DE); Christian Trommer, Ilmenau (DE)

(73) Assignee: avateramedical GmbH, Jena (DE)

( * ) Notice: Subject to any disclaimer, the term of this patent is extended or adjusted under 35 U.S.C. 154(b) by 60 days.

(21) Appl. No.: 16/059,945

(22) Filed: Aug. 9, 2018

(65) Prior Publication Data
US 2019/0046279 A1 Feb. 14, 2019

(30) Foreign Application Priority Data
Aug. 9, 2017 (DE) .......................... 102017118126.1

(51) Int. Cl.
*A61B 34/30* (2016.01)
*B25J 9/00* (2006.01)
(Continued)

(52) U.S. Cl.
CPC .............. *A61B 34/30* (2016.02); *A61B 34/70* (2016.02); *A61B 90/50* (2016.02); *B25J 9/0009* (2013.01); *B25J 9/0084* (2013.01); *B25J 9/08* (2013.01); *A61B 2017/00199* (2013.01); *A61B 2017/00477* (2013.01); *A61B 2034/305* (2016.02); *A61B 2090/508* (2016.02)

(58) Field of Classification Search
CPC .............. A61B 34/30; A61B 2034/304; A61B 2034/305; A61B 2017/00199; A61B 34/70; A61B 90/50; B25J 9/009; B25J 9/0084

See application file for complete search history.

(56) References Cited

U.S. PATENT DOCUMENTS 5,108,140 A * 4/1992 Bartholet ............. B25J 15/0009
294/106
6,788,018 B1 * 9/2004 Blumenkranz ........ B25J 9/0018
128/DIG. 7

(Continued)

FOREIGN PATENT DOCUMENTS

CN 106236276 A 12/2016
DE 10 2013 004 459 A1 6/2014
(Continued)

*Primary Examiner* — Alexander J Orkin
(74) *Attorney, Agent, or Firm* — Christensen, Fonder, Dardi & Herbert PLLC (57) ABSTRACT

A robotic surgical system comprising a supporting column, a plurality of manipulator arms, a control device and a boom. The boom is connected at one end to the supporting column and at the other end includes a plurality of coupling devices for coupling the manipulator arms to the booms Depending on the position of the respective manipulator arm on the boom, some manipulator arms may be connected via first coupling devices with first coupling mechanisms to the boom, and other arms may be connected via second coupling devices to the boom. The first coupling mechanism comprises a first pivot joint. The second coupling mechanism comprises a second pivot joint, a third pivot joint and a linkage part connecting the pivot joints. The axes of rotation of the second and third pivot joints are spaced apart by the linkage part and lie parallel to each other.

14 Claims, 6 Drawing Sheets

(51) Int. Cl.
    *B25J 9/08*     (2006.01)
    *A61B 34/00*     (2016.01)
    *A61B 90/50*     (2016.01)
    *A61B 17/00*     (2006.01)

(56) References Cited

U.S. PATENT DOCUMENTS

| | | |
|---|---|---|
| 6,837,883 B2 | 1/2005 | Moll et al. |
| 8,888,789 B2 | 11/2014 | Prisco et al. |
| 9,795,454 B2 | 10/2017 | Seeber et al. |
| 2009/0048612 A1* | 2/2009 | Farritor .................. A61B 34/30 606/130 |
| 2009/0209976 A1* | 8/2009 | Rosielle ................ A61B 34/37 606/130 |
| 2013/0144307 A1* | 6/2013 | Jeong ..................... B25J 9/0087 606/130 |
| 2014/0052153 A1 | 2/2014 | Griffiths et al. |
| 2014/0180308 A1* | 6/2014 | von Grunberg ....... A61B 90/11 606/130 |
| 2014/0257328 A1* | 9/2014 | Kim ..................... A61B 90/361 606/130 |
| 2015/0257840 A1* | 9/2015 | Mohr ..................... A61B 34/37 606/130 |
| 2015/0297299 A1* | 10/2015 | Yeung ................. A61B 1/0016 600/102 |
| 2017/0079730 A1 | 3/2017 | Azizian et al. |
| 2017/0274533 A1 | 9/2017 | Berghofer et al. |

FOREIGN PATENT DOCUMENTS

| | | |
|---|---|---|
| WO | WO 2016/023635 A1 | 2/2016 |
| WO | WO 2018/059039 A1 | 4/2018 |

\* cited by examiner

ROBOTIC SURGICAL SYSTEM

PRIORITY CLAIM

The present application claims priority to German Patent Application No. 10 2017 118 126.1, filed on Aug. 9, 2017, which said application is incorporated by reference in its entirety herein.

FIELD OF THE INVENTION

The invention relates to a robotic surgical system. Such a surgical system comprises an optionally height-adjustable supporting column, a number of manipulator arms and a boom which is connected at one of its ends to the supporting column and at the other of its ends has means for coupling the manipulator arms. The robotic surgical system also comprises a control device for controlling the robotic surgical system, in particular for pre-positioning the manipulator arms before an operation.

BACKGROUND OF THE INVENTION

In a robotic surgical system, the operator, the surgeon, operates one or more robotically controlled arms, which hold instruments, in order to carry out individual steps of an operation. The surgeon controls the manipulator arms of the system via an operator console or by corresponding movements via a suitable coupling mechanism which converts movements of the surgeon's hands into movements of the corresponding instrument. The manipulator arms are multi-part systems, in which the individual parts are connected to each other via joints. A portion of the parts serves to position the manipulator arm relative to other manipulator arms of the same robotic system so that the manipulator arms do not impede each other. This portion of the parts is also called an adjusting device. The described positioning is effected before the operation and is therefore also called a pre-positioning. Another portion of the parts serves to position and guide the tool on the object, thus for example to position a surgical instrument or an endoscope in the region of an opening in the tissue cover of a patient. This portion of the parts is also called an instrument-carrier device. The arm parts are connected to each other in a kinematic sense as an open kinematic chain, as the tool, not a further joint, sits on the last part. All the other parts are connected to each other via joints in the manner of a chain.

At the end of the chain that does not hold the instrument, the chain is connected to a carrier device—also comprising the supporting column and the boom—via a coupling device. The carrier device serves in particular to hold the individual manipulator arms, but the electrical lines, which serve to supply power to and control the manipulator arms, are also guided in them. The instrument-carrier devices themselves, with the instruments, operate in an area that is to be kept sterile, lines to them must not be exposed.

The manipulator arms are actuated individually, but are coupled to the common carrier device, with the result that a surgeon or medical assistant also continues to have easy access to the patient being treated. Because of the mass of the arms, the carrier device, if it is mounted on the floor, must be dimensioned correspondingly large, in order to generate a sufficient counter weight for the manipulator arms. On the other hand, the surgical system is also to be kept as compact as possible, in order to guarantee a good accessibility to the patient and easy handling of the surgical system, for example when it has to be moved.

In order to make a maximum movability of the manipulator arms of the surgical system possible, they should ideally be suspended independently of each other, which is, however, too complex in practice and brings with it other disadvantages. For example, four manipulator arms could be arranged at fixed positions on the operating table. However, this makes it difficult for staff to access the patient. In practice therefore a common suspension of the—usually four—manipulator arms is always used, but in certain circumstances this can have the result that the manipulator arms impede each other, or are not as freely adjustable as would be desirable for optimally carrying out the treatment.

In the state of the art, for the suspension of the manipulator arms, various devices are known which thus realize means for coupling the manipulator arms in different ways.

In the surgical system disclosed in DE 10 2013 004 459 A1 with four manipulator arms, the manipulator arms are connected to a boom with a T-shaped or crossbeam-type structure via identical coupling devices and can be pivoted about the longitudinal axis of the crossbeam. The crossbeam itself has joints which allow a tilting relative to the longitudinal axis of the crossbeam by approximately 30°. However, in certain circumstances this leads to collisions between the arms during the surgical procedure. The manipulator arm parts forming the closed end of the kinematic chain are always evenly spaced apart along the longitudinal axis of the crossbeam in the region of the coupling points on the carrier device in relation to this axis.

U.S. Pat. No. 6,837,883 B2 describes a robotic surgical system in which four manipulator arms are attached individually to the four sides of a cuboidal column, the arms are individually height-adjustable. The four arms here are thus not secured to a common boom, but individually to the supporting column, on which the arms are individually height-adjustable. The supporting column as a whole therefore need not be height-adjustable. The rear arm here has a further arm segment in order to compensate for the greater distance from the patient. In order to be able to fulfill the functionality of pre-positioning, the arm segments must be comparatively long, therefore the device as a whole is very bulky, which makes it difficult to handle.

A further robotic surgical system is described in US 2014/0052153 A1. The supporting column here is height-adjustable, a horizontally protruding boom is attached to the supporting column, and it is securely connected with one of its sides to the supporting column, as shown for example in FIG. 8 of US 2014/0052153 A1. A so-called orienting platform is arranged on the free side of the boom. Four arm booms, which can be individually pivoted in the plane and adapted in terms of their length, are arranged on the orienting platform, protruding in the horizontal direction—more precisely in the plane of the platform. In addition, the orienting platform itself is also rotatable about a vertical axis of rotation. Finally, the manipulator arms of the robotic surgical system are secured to the free ends of the arm booms, wherein the first arm part, which is connected to the respective arm boom, is oriented with its longitudinal axis in the vertical direction and is connected to the arm boom rotatably about this axis. The orienting platform is moreover tiltable with respect to the horizontal base plane, which leads to a change in position of the axes of rotation, arm booms, orientations and arm directions just described. Although this structure offers many possible settings, it is constructed in a very complex manner, which requires firstly a production which is technically complex and expensive and secondly a long familiarization period for the operator because of the many possible settings.

SUMMARY OF THE INVENTION

An object of the invention is therefore to develop a robotic surgical system of the type described at the beginning to the extent that with a coupling device for the manipulator arms that is designed as simply as possible, a sufficiently great freedom of movement for the arms, which does not impede the surgeon and prevents collisions during operation, is nevertheless made possible. The system here is moreover to be built as compact as possible, with the result that it requires little space in use.

This object is achieved for a robotic surgical system of the type described at the beginning in that, depending on the position of the respective manipulator arm on the boom, a first portion of the number of manipulator arms is connected to the boom via first coupling devices with first coupling mechanisms and a second portion of the number of manipulator arms are connected to the boom via second coupling devices with second coupling mechanisms. Different manipulator arms can thus be coupled to the boom with different coupling devices. The selection of the coupling device to be used in each case is effected here in dependence on the position of the respective manipulator arm on the boom. By not using the same coupling device for all the manipulator arms, as is the case in the state of the art, a greater flexibility is obtained. However, as the coupling devices are restricted to a relatively small installation space, as they are all attached to the boom, this gain in flexibility is not at the expense of the compactness.

The coupling device here is interposed between the boom and the manipulator arm, and thus connects these two. The first coupling mechanism in the first coupling device here consists of a first pivot joint. In a compact version, between the boom and the manipulator arm coupled thereto via the first coupling device, there is a sliding plane perpendicular to the axis of rotation of the first pivot joint, but the spacing can also be larger, with the result that the configuration of the boom impedes the movement of the manipulator arm as little as possible. The second coupling mechanism consists of a second pivot joint, a third pivot joint and a linkage part, which connects the second and the third pivot joint to each other. The axes of rotation of the second pivot joint and of the third pivot joint lie parallel to each other, by means of the linkage part, moreover, a spacing between the two axes of rotation is, on the one hand, produced perpendicular thereto, i.e. by means of the linkage part the axes of rotation of the second and of the third pivot joint, and thus the two pivot joints, are spaced apart from each other in a direction perpendicular to the axes of rotation. On the other hand, it is also achieved by means of the linkage part that a spacing of the pivot joints in the direction along the axes of rotation is produced, i.e. by means of the linkage part the two pivot joints are also spaced apart from each other in the direction along the axes of rotation.

The second pivot joint connects the boom to the linkage part and the third pivot joint connects the linkage part to the manipulator arm. An offset of the two pivot joints relative to each other along a direction parallel to the axes of rotation is produced by the linkage part, with the result that the rotations about the second and the third pivot joint can be effected independently of each other and in particular in principle not influenced by each other. In the case of two pivot joints designed as hinges, the linkage part is located precisely in between, with the result that the rotations about the two joints in principle cannot impede each other. In practice, however, the freedom of movement is limited by the dimensions of the boom and by the other manipulator arms. However, the vertical offset of the second and third pivot joints relative to each other, which is produced by the linkage part, is important, with the result that the manipulator arm attached to the linkage part obtains as great as possible a freedom of movement.

The linkage part of the second coupling mechanism can be designed, for example, as a rod-shaped or plate-shaped body. It advantageously has two sides opposite each other, which are spaced apart along the axes of rotation of the second or third pivot joint; these sides are also called upper and lower side, without limiting the generality. The axes of rotation of the second and third pivot joints both also run through the linkage part and push through the upper and lower side respectively. The spacing between the two axes of rotation here should expediently be chosen to be as large as possible, in order to obtain a maximum movement and setting possibility. The second pivot joint connects the linkage part on one of the two opposite sides to the boom. The third pivot joint connects the linkage part on the other of the two opposite sides to the manipulator arm.

Which manipulator arm is coupled to the boom with which coupling device depends on the position of the coupling device on the boom. If, for example, the coupling devices are arranged on the boom in the manner of a row, for example formed in a row on an optional crossbeam, it is advantageous if the manipulator arms are connected to the boom by means of the second coupling devices at least at the two end positions of the row. In this way, in particular the exterior arms, which lie slightly further away from the site of treatment, obtain a greater freedom of movement.

However, at its end facing away from the supporting column the boom is preferably not formed in a row, for example with a crossbeam, but as a two-pronged, Y-shaped fork structure, wherein on the prongs, particularly preferably at their free or loose ends, in each case a manipulator arm is connected to the boom by means of a second coupling device. The outer manipulator arms are thereby positioned slightly closer to the site of treatment and need not grip around the inner arms. An even more compact construction is thus made possible.

The rotation of the manipulator arms about the axes of rotation of the first, second and third pivot joints is to achieve a pre-positioning of the manipulator arms for the operation, with the result that subsequently only the instrument-carrier device is moved during the operation. For this purpose it is advantageous if the pivot joints are motor-driven and can all be adjusted and fixed in a motorized manner, in particular if in the case of the second coupling mechanism the position of the third pivot joint relative to the second pivot joint can be adjusted in a motorized manner and/or can be fixed via a brake that can be positioned preferably in a motorized manner.

The supporting column can, as is usual in the state of the art, be floor-mounted, but in a particularly preferred embodiment it is ceiling-mounted, i.e. it hangs down from the ceiling. This significantly improves the possibilities for the medical staff to access the patient.

The boom can form a right angle with the supporting column, but it can also be formed at least partially arched, the angle enclosed by the arch is then preferably likewise 90°. The arch shape also contributes to a more compact construction. In particular if the boom is formed protruding from the supporting column, it can be advantageous if the boom is also adjustable in terms of its length, in order to be able to position the manipulator arms even closer to patients, without the structure of the supporting column interfering.

It is understood that the features named above and those yet to be explained below are applicable not only in the stated combinations, but also in other combinations or alone, without departing from the scope of the present invention.

BRIEF DESCRIPTION OF THE DRAWINGS

The invention is explained in even more detail below by way of example with reference to the attached drawings, which also disclose features essential to the invention. There are shown in.

DETAILED DESCRIPTION

Figure 1A:
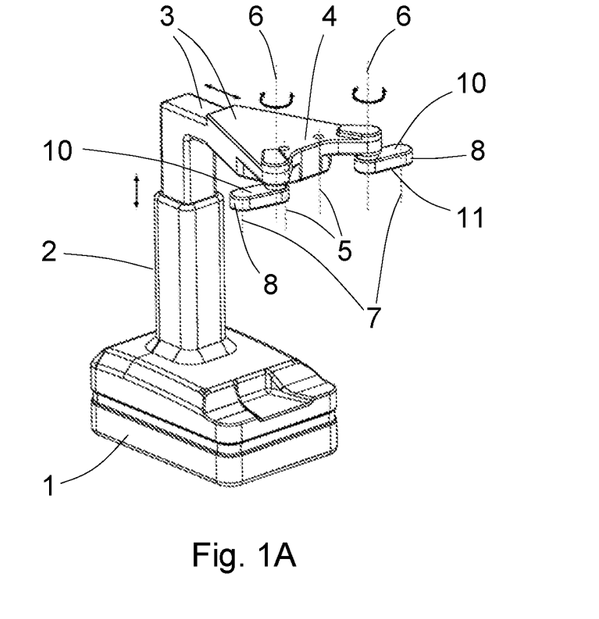
FIG. 1A, which is a perspective view of a structure of a supporting structure for a robotic surgical system, according to an embodiment.

FIG. 1A shows an example supporting structure for a robotic surgical system. This comprises a base 1, which can be weighed down internally by weights and/or can also be screwed to the floor or connected thereto in another way. A supporting column 2, which is advantageously adjustable in terms of its height here, rises out of the base 1. At the upper end of the supporting column 2, a boom 3 is formed protruding from the supporting column at an angle of 90°. Of course, other angles are likewise possible. The boom 3 here is designed straight and adjustable in terms of its length. At its free end facing away from the supporting column 2, the boom 3 is formed as a two-pronged, Y-shaped fork structure 4. At this end the boom 3 has means for coupling manipulator arms with a number or plurality of coupling devices for the manipulator arms corresponding to the number or plurality of manipulator arms. Not shown is a control device for controlling the robotic surgical system, which nevertheless forms a component of the system. As an alternative to the formation as a fork structure 4, the boom 3 can also have a crossbeam-type structure, a bar, on which the coupling devices are lined up, at its free end.

Depending on the position of the respective manipulator arm on the boom 3, a first portion of the number of manipulator arms is connected to the boom 3 via first coupling devices with first coupling mechanisms. A second portion of the number of manipulator arms is connected to the boom 3 via second coupling devices with second coupling mechanisms. The first coupling mechanism consists of a first pivot joint 5, here correspondingly indicated by dashed lines. The second coupling mechanism consists of a second pivot joint 6 and a third pivot joint 7 as well as a linkage part 8 connecting the two pivot joints 6, 7. All the coupling devices can comprise motorized positioning drives for the first, second and/or third pivot joint 5, 6, 7. The axes of rotation of the second and third pivot joints 6, 7 lie parallel to each other and are spaced apart from each other in a direction perpendicular to the axes of rotation by means of the linkage part 8. The linkage part 8 moreover ensures that the second pivot joint 6 and the third pivot joint 7 are also spaced apart from each other in the direction of the axes of rotation, i.e. along them, with the result that rotational movements about the second and third pivot joints 6, 7 in principle do not impede each other.

Figure 1B:
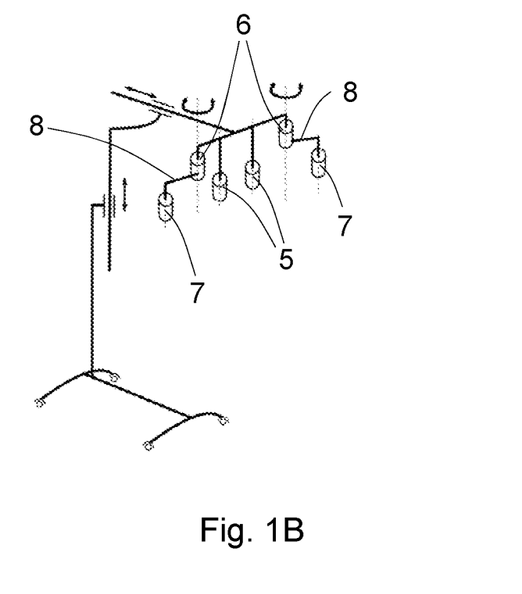
FIG. 1B, which is a depiction of a structure of the parts of the supporting structure of FIG. 1A.

This is shown again in FIG. 1B in an abstract manner and for illustration; here the structures are omitted and only the structure of the parts for the movements, which can be impressed on the coupling devices, are represented. For ease of understanding, the same reference numbers as in FIG. 1A have been chosen, but they are to be understood in an abstract manner here. The first pivot joints 5 here are drawn in at the same height as the second pivot joints 6, whereas they are arranged at the same height as the third pivot joints 7 in the variant shown in FIG. 1A, with the result that all the manipulator arms couple on at the same height.

Figure 1C:
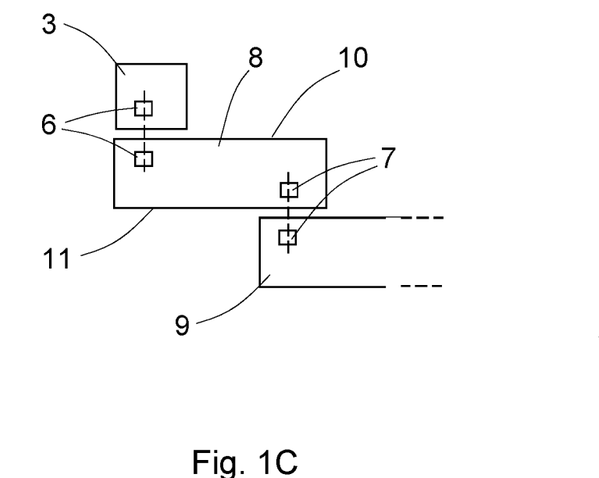
FIG. 1C, which is a depiction of a second coupling mechanism.

FIG. 1C explains the second coupling mechanism in somewhat more detail. The boom 3 is connected to the linkage part 8 via the second pivot joint 6. The linkage part 8 for its part is connected to a manipulator arm 9 via the third pivot joint 7. On the one hand, the linkage part 8 ensures that the axes of rotation of the second pivot joint 6 and of the third pivot joint 7 are spaced apart from each other in a direction perpendicular to the axes of rotation. On the other hand, the linkage part 8 also ensures that an offset is introduced between the second pivot joint 6 and the third pivot joint 7 along the axes of rotation, which ensures that the rotational movements of the two joints in principle do not impede each other, i.e. the rotation of the manipulator arm 9 about the axis of rotation of the third pivot joint 7 is not impeded by the rotation of the linkage part 8 about the axis of rotation of the second pivot joint 6, unless impeding occurs due to the dimensions of the boom 3 etc.

The linkage part 8 in FIG. 1C is formed as a three-dimensional body with two opposite sides, here an upper side 10 and a lower side 11. In principle, the linkage part 8 can also be formed as a flat, plate-shaped body, if this is capable of withstanding the loads due to the mass of the manipulator arms 9 to be attached thereto. The boom 3 is connected on the upper side 10 of the linkage part 8 to the latter via the second pivot joint 6, the manipulator arm is connected on the lower side 11 of the linkage part 8 to the latter via the third pivot joint 7. In the compact structure shown here, an air gap is located in each case between the boom 3 and the linkage part 8 and between the linkage part 8 and the manipulator arm 9. In an even more compact design, the air gaps can also be formed as first and second sliding planes. The two sliding planes are spaced apart from each other by the dimensions of the linkage part 8 along the axes of rotation of the pivot joints 6, 7. The linkage part can also be formed rod-shaped with a round cross section. The upper side and the lower side then correspond to the respective upper and lower arched surfaces with in each case an angle in cross section of 180°. Any desired intermediate shapes and other shapes are likewise possible, the two opposite sides can also be formed as almost one-dimensional line structures, for example in the case of a plate-shaped body, the large surfaces of which have a normal direction perpendicular to the axes of rotation.

Figure 1D:
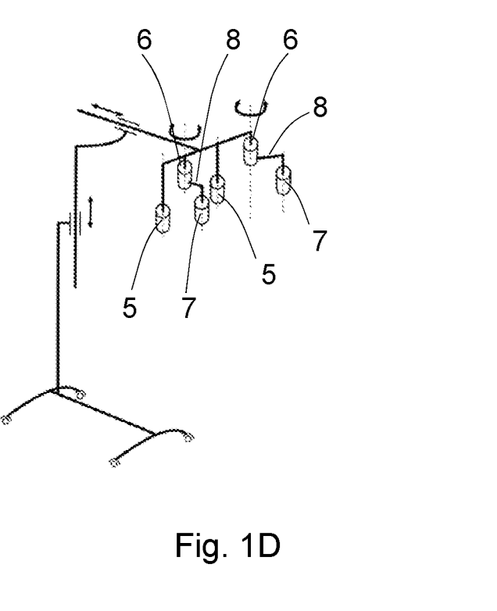
FIG. 1D, which is a depiction of a modified structure of the parts for a supporting structure.

FIG. 1D shows a configuration slightly modified with respect to FIG. 1A and FIG. 1B. While the configuration shown in FIGS. 1A, 1B is symmetrical in such a way that the—in this case two—manipulator arms 9 which form the second portion of the number of manipulator arms 9 are arranged on the outside, and the rest of the manipulator arms 9 are arranged on the inside, the configuration shown in FIG. 1D thus corresponds to an alternating arrangement, in which one manipulator arm 9 of the first number of manipulator arms 9 is arranged exclusively next to manipulator arms 9 of the second number of manipulator arms 9. In addition, further possible arrangements of the first and second numbers of manipulator arms 9 are also possible, for example an arrangement complementary to FIG. 1A, B, i.e. an arrangement in which the first number of manipulator arms 9 is arranged on the outside and the second number of manipulator arms is arranged on the inside. The more manipulator arms 9 the robotic surgical system comprises, the more possibilities there are for the arrangement of the first and second numbers of manipulator arms 9, culminating in an arrangement that is statistical or determined as particularly advantageous as a result of a calculational process with minimal impeding of each other by the movements of the manipulator arms 9.

Figure 2:
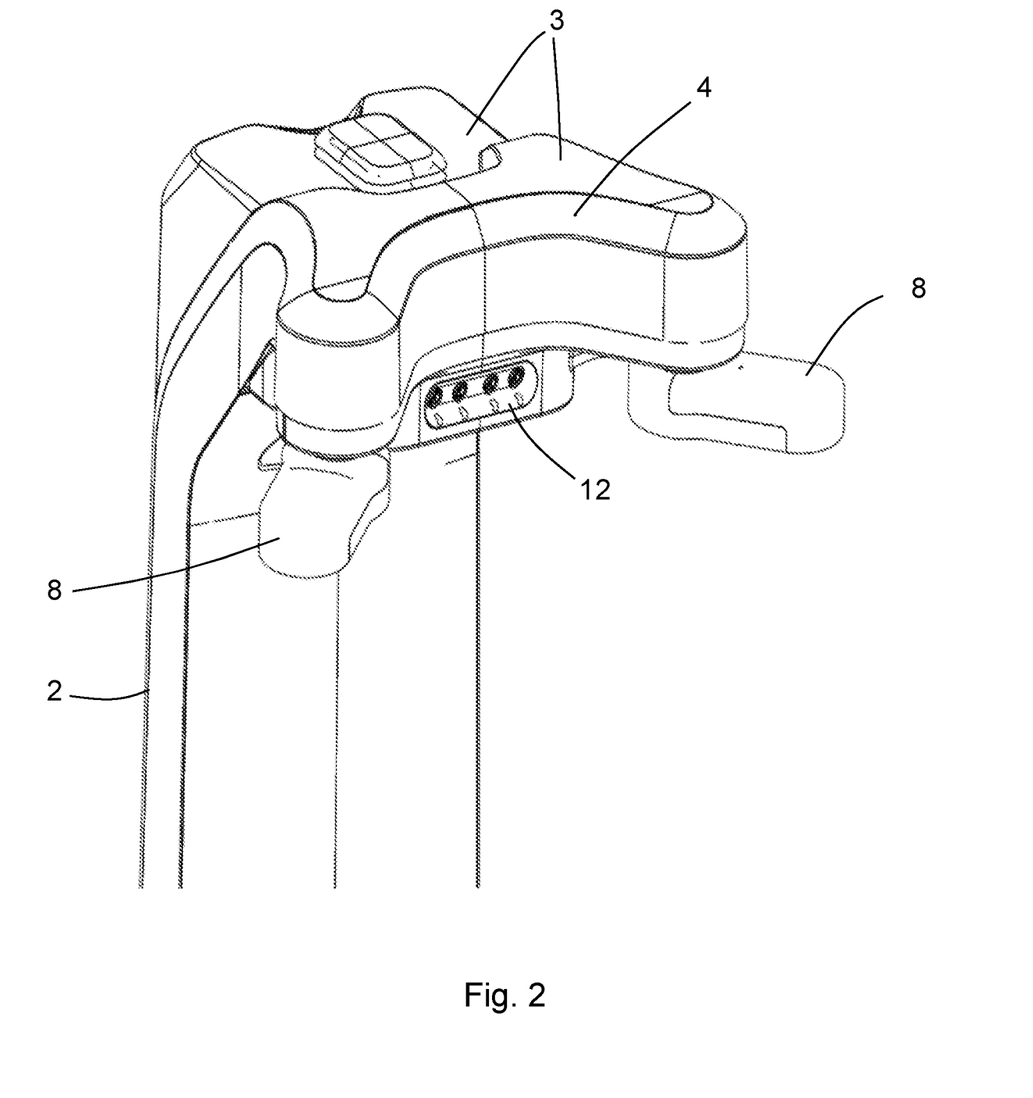
FIG. 2, which is a perspective view of a section of a supporting structure for a robotic surgical system, according to an embodiment.

FIG. 2 shows a similar embodiment to FIG. 1A, but here the boom 3 is not adjustable in terms of its length. FIG. 2 shows a section of a supporting system, the base is not represented here. Moreover, outputs of a bus system 12 are shown here, which serve to couple in the controller of the manipulator arms. The position of the third pivot joint 7 relative to the second pivot joint 6 and the positions of all the manipulator arms 9 can be adjusted in a motorized manner by means of the controller, additionally the relative positions of the third pivot joints 7 can be fixed via a brake that can be positioned in a motorized manner.

Figure 3:
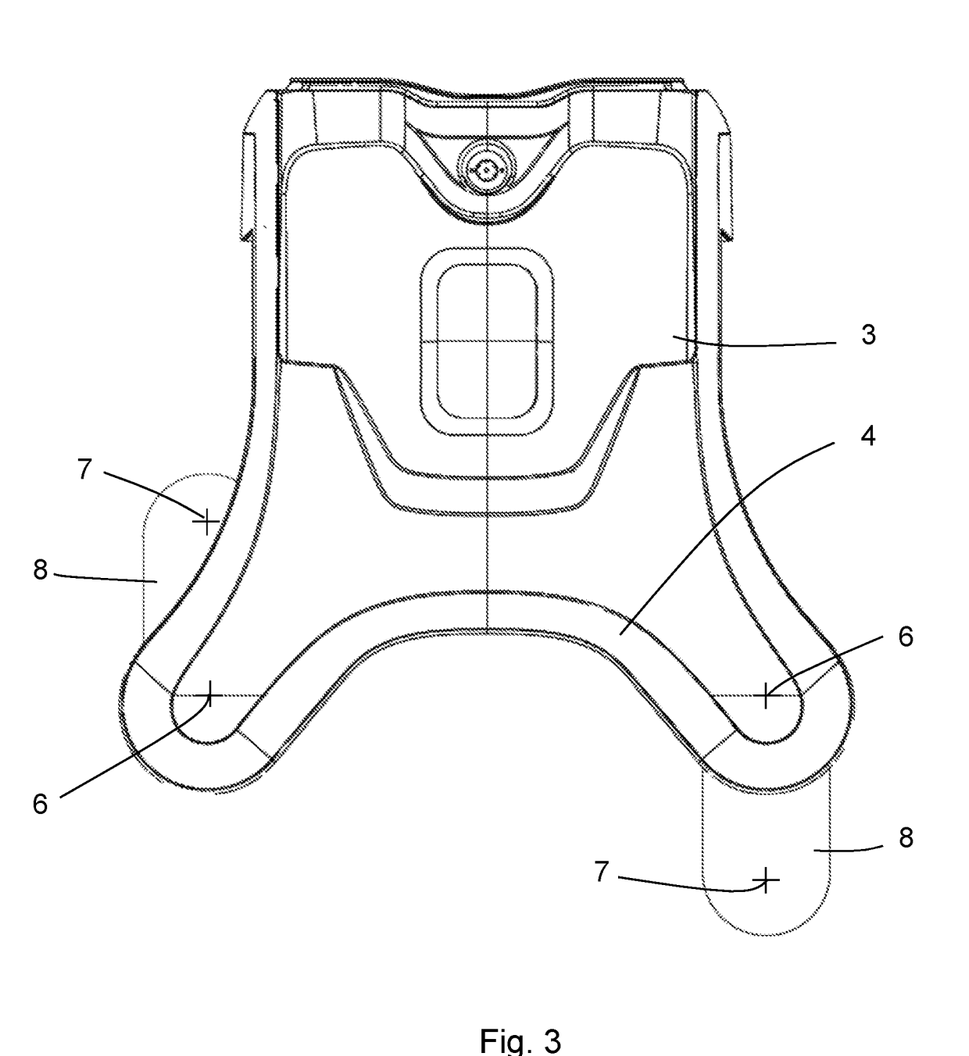
FIG. 3, which is a top view of the system shown in FIG. 2.

FIG. 3 shows the supporting system from FIG. 2 in a top view from above; here the linkage parts 8 are shown in two extreme positions, in order to illustrate the movement possibilities. The positions of the second pivot joints 6 and the current positions of the third pivot joints 7 are indicated by crosses.

Figure 4:
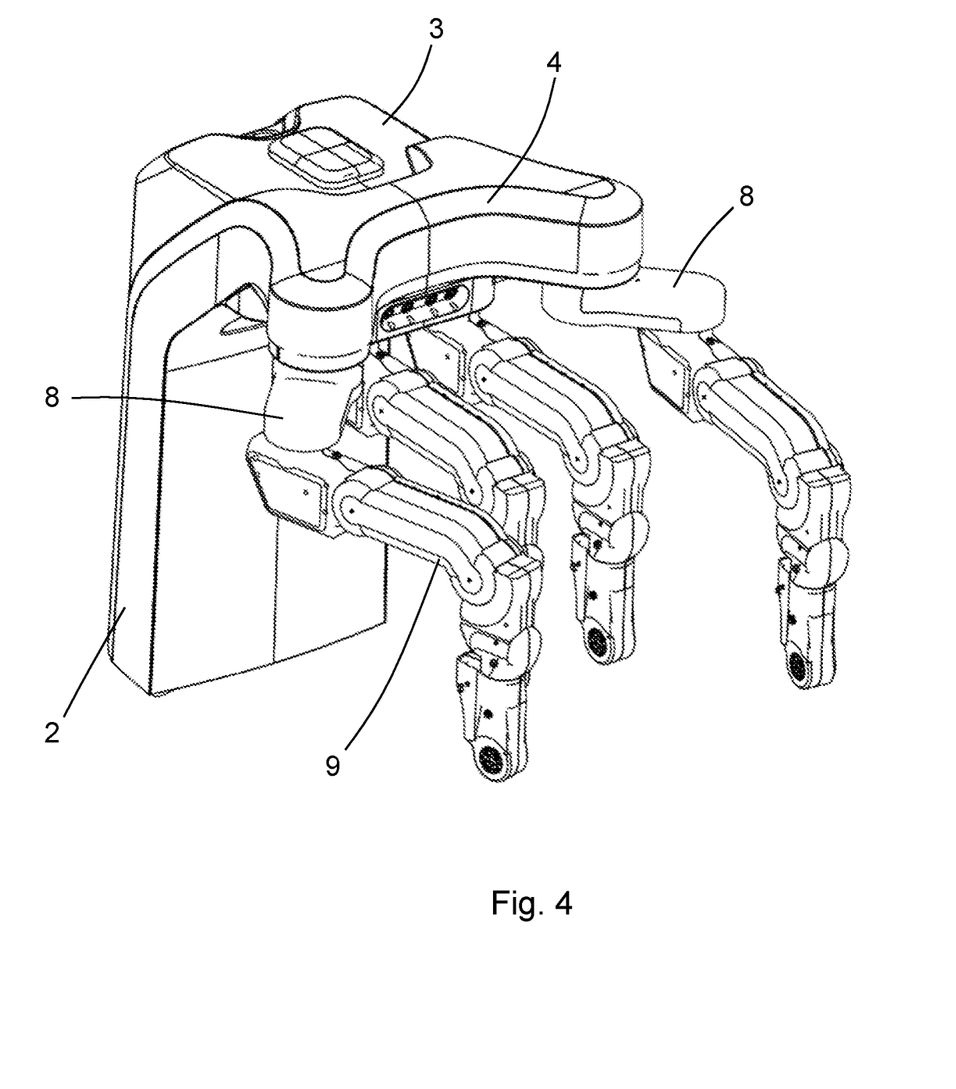
FIG. 4, which is a perspective view of parts of manipulator arms coupled to the supporting structure without an instrument-carrier device.

Finally, FIG. 4 shows a section of the robotic surgical system, the supporting structure of which was represented in FIGS. 2 and 3, here with parts of coupled manipulator arms 9. The parts of the manipulator arms 9 shown here serve for the pre-positioning, an instrument-carrier device is yet to be coupled to the parts.

Figure 5:
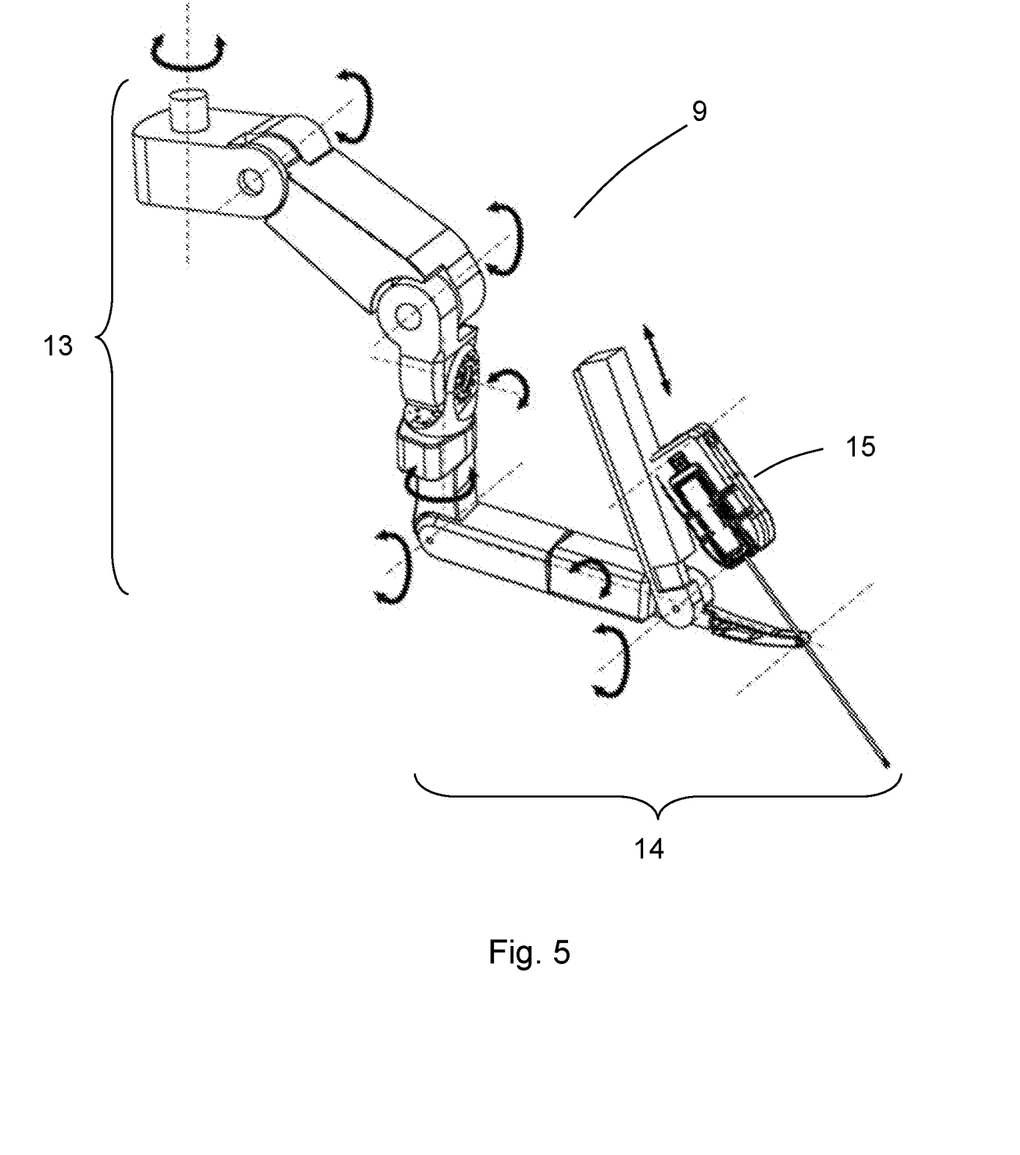
FIG. 5, which is a perspective view of a manipulator arm with instrument-carrier device, according to an embodiment.

For the sake of completeness, a complete manipulator arm 9 is shown in FIG. 5. The arm is a multi-part system, which corresponds to a loose kinematic chain. One portion of the parts forms a positioning device 13, indicated by the curly brackets on the left in the drawing, the other portion of the parts forms the instrument-carrier device 14 with instrument holder 15 coupled thereto.

Figure 6A:
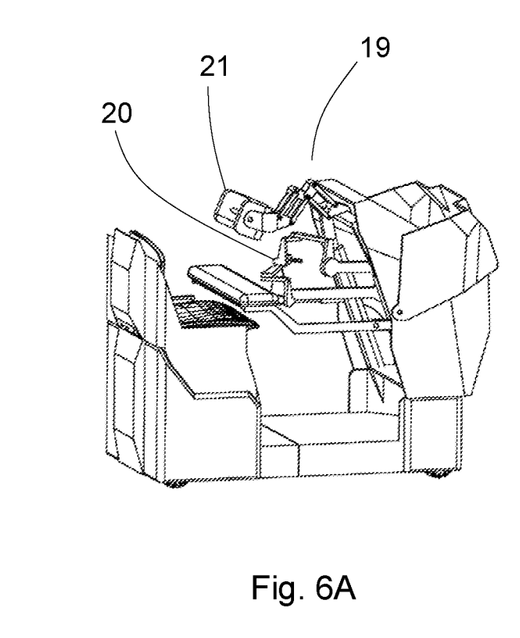
FIG. 6A, which is a control device of a robotic surgical system, according to an embodiment.
Figure 6B:
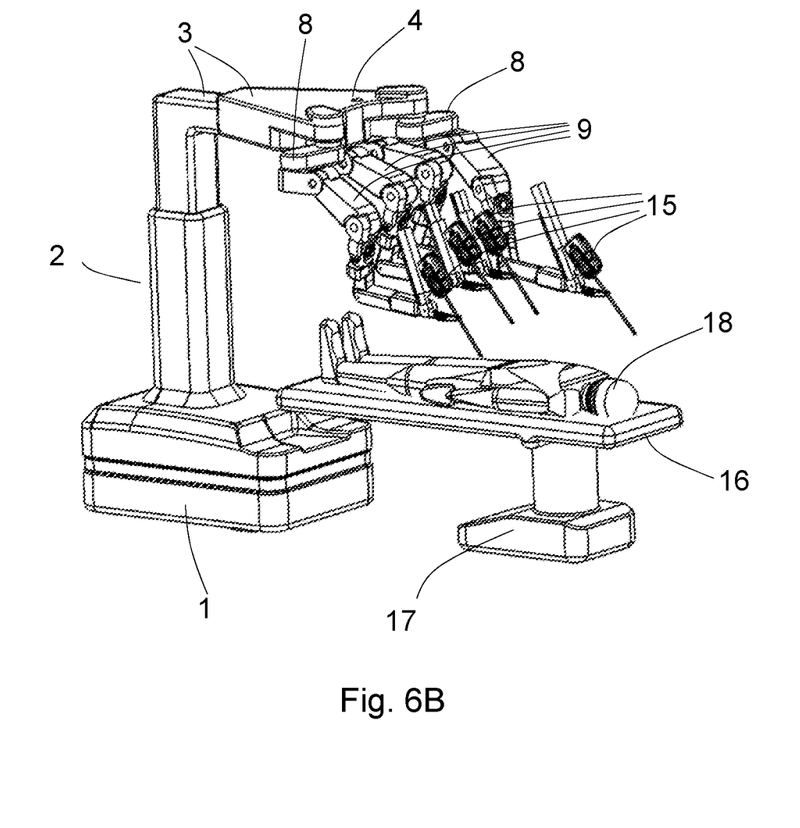
FIG. 6B, which is a robotic surgical system with operating table, according to an embodiment.

Finally, FIGS. 6A, B show a robotic surgical system in an overall view. The supporting structure of the robotic surgical system is shown in FIG. 6B, which, analogously to FIG. 1A, comprises a base 1, a supporting column 2 with a boom 3 protruding therefrom and a fork structure 4 at the free end of the boom 3. On the boom 3 with the fork structure 4, a total of four manipulator arms 9 with instrument holders 15 are arranged, the outer two again form the second number of manipulator arms 9. These are in an idle position here and are not yet positioned for an operation. Underneath the manipulator arms 9 with the instrument holders 15, an operating table 16 is arranged on a table base 17, on which a person 18 to be operated on is located. The operating table 16 can be rotatably mounted on the table base 17. In addition, the supporting structure of the robotic surgical system and the operating table 16 can advantageously also be moved translationally relative to each other.

The robotic surgical system also has a control device 19 for controlling it, which is shown in FIG. 6A and is likewise moveable, here displaceable, relative to the supporting structure. It is operated by a specially trained surgeon, and the movements of the surgeon on handles 20 of the control device 19 are transmitted to the manipulator arms 9 or to instruments held in the instrument holders 15. In the process the surgeon can monitor the field of operation with the aid of a viewing device 21.

The robotic surgical system described above can be built compact and requires less space compared with conventional surgical systems because of its coupling structure for the manipulator arms, but nonetheless enables a surgeon to position the manipulator arms without collisions.

LIST OF REFERENCE NUMBERS

1 Base
2 Supporting column
3 Boom
4 Fork structure
5 First pivot joint
6 Second pivot joint
7 Third pivot joint
8 Linkage part
9 Manipulator arm
10 Upper side
11 Lower side
12 Bus system
13 Positioning device
14 Instrument-carrier device
15 Instrument holder
16 Operating table
17 Table base
18 Person
19 Control device
20 Handles
21 Viewing device

The invention claimed is:
1. A robotic surgical system, comprising:
a supporting column,
a plurality of manipulator arms, including a first set of manipulator arms and a second set of manipulator arms, each manipulator arm of the first and second sets of manipulator arms configured as a loose kinematic chain,
a boom connected at one end to the supporting column and at another end including a plurality of coupling mechanisms including first and second coupling mechanisms configured to couple the plurality of manipulator arms to the boom, wherein the boom forms a structure at an end distal to the supporting column that includes two projections, and
a control device for controlling the robotic surgical system,
wherein the first set of manipulator arms are coupled to the boom via the first coupling mechanisms, and the second set of manipulator arms are coupled to the boom via the second coupling mechanisms, one of the second manipulator arms being connected to one of the two projections of the boom by one of the second coupling mechanisms, and another of the second manipulator arms being connected to the other of the two projections of the boom by another of the second coupling mechanisms,
wherein each of the first coupling mechanisms consists of a first pivot joint, and
wherein each of the second coupling mechanisms consists of a second pivot joint, a third pivot joint and a unitary linkage part connecting the second pivot joint and the third pivot joint, wherein the second pivot joint and the third pivot joint have axes of rotation lying parallel to each other and are spaced apart from each other by the linkage part both in a direction along the axes of rotation and in a direction perpendicular to the axes of rotation.

2. The robotic surgical system according to claim 1, wherein the linkage part of the second coupling mechanism has two opposite sides which are spaced apart from each other along the axes of rotation of the second pivot joint and of the third pivot joint, wherein the second pivot joint connects the linkage part to the boom on one of the two opposite sides and the third pivot joint connects the linkage part to a manipulator arm of the second set of manipulator arms on the other of the two opposite sides.

3. The robotic surgical system according to claim 1, wherein the second coupling mechanism is configured such that a position of the third pivot joint relative to the second pivot joint is configured to be adjusted in a motorized manner.

4. The robotic surgical system according to claim 1, wherein the supporting column is mounted on a ceiling.

5. The robotic surgical system according to claim 1, wherein the boom is formed at least partially arched.

6. The robotic surgical system according to one of claim 1, wherein the boom is formed as protruding from the supporting column at an angle of 90°.

7. The robotic surgical system according to claim 1, wherein the boom is adjustable in terms of its length.

8. The robotic surgical system according to claim 1, wherein the second coupling mechanism is configured such that a position of the third pivot joint relative to the second pivot joint is configured to be fixed via a brake that can be positioned in a motorized manner.

9. The robotic surgical system according to claim 1, wherein the second coupling mechanism is configured such that a position of the third pivot joint relative to the second pivot joint is configured to be adjusted in a motorized manner and is configured to be fixed via a brake that can be positioned in a motorized manner.

10. The robotic surgical system according to claim 1, wherein the boom is formed at least partially arched, and wherein an angle enclosed by the arch is a 90° angle.

11. The robotic surgical system according to claim 1, wherein the structure formed by the boom that includes two projections is a pronged, Y-shaped fork structure.

12. The robotic surgical system according to claim 1, wherein the structure formed by the boom that includes two projections is a cross-beam type structure that forms a bar.

13. The robotic surgical system according to claim 1, wherein the linkage part is formed as a rod-shaped body.

14. The robotic surgical system according to claim 1, wherein the linkage part is formed as a plate-shaped body.

* * * * *